US011109984B2

(12) United States Patent
Termanini et al.

(10) Patent No.: US 11,109,984 B2
(45) Date of Patent: *Sep. 7, 2021

(54) TOOL AND METHOD FOR SEPARATING A FEMORAL CUP FROM AN ACETABULAR BALL IN AN IMPLANTED HIP PROSTHESIS

(71) Applicant: HIP INNOVATION TECHNOLOGY, LLC., Boca Raton, FL (US)

(72) Inventors: Zafer Termanini, Port Saint Lucie, FL (US); Brian Vanhiel, Smyrna, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/160,628

(22) Filed: Oct. 15, 2018

(65) Prior Publication Data
US 2019/0105182 A1 Apr. 11, 2019

Related U.S. Application Data

(62) Division of application No. 15/742,192, filed as application No. PCT/US2016/042424 on Jul. 15, 2016, now Pat. No. 11,020,242.

(Continued)

(51) Int. Cl.
*A61F 2/46* (2006.01)
*A61F 2/32* (2006.01)
*A61F 2/30* (2006.01)
*A61F 2/34* (2006.01)
*A61F 2/36* (2006.01)

(52) U.S. Cl.
CPC .............. *A61F 2/4637* (2013.01); *A61F 2/32* (2013.01); *A61F 2/4607* (2013.01); *A61F 2/4609* (2013.01); *A61F 2/4603* (2013.01); *A61F 2002/30538* (2013.01); *A61F 2002/3483* (2013.01); *A61F 2002/3615* (2013.01);
(Continued)

(58) Field of Classification Search
CPC .... A61F 2/4637; A61F 2/4607; A61F 2/4609; A61F 2002/4641; A61F 2002/4619
See application file for complete search history.

(56) References Cited

U.S. PATENT DOCUMENTS 3,801,989 A * 4/1974 McKee ..................... A61F 2/32
 623/22.12
4,457,306 A 7/1984 Borzone
(Continued)

FOREIGN PATENT DOCUMENTS

CN 102905649 A 1/2013

OTHER PUBLICATIONS

International Search Report for corresponding application PCT/US2016/042424 dated Oct. 4, 2016.
(Continued)

*Primary Examiner* — Amy R Sipp

(57) ABSTRACT

Surgical tools which are used to separate from one another a femoral cup and an acetabular ball in an implanted hip replacement prosthesis. At its distal end, elements of the surgical tool engage the femoral cup and the acetabular cup. When proximal handles of the tool are squeezed toward one another, the engagement elements move away from one another. Thus, a surgeon is able to separate the femoral cup and the acetabular ball from one another without pulling the acetabular cup away from the acetabulum or the femoral cup and/or femoral implant away from the femur, thereby accomplishing the separation without disrupting any bone ingrowth.

8 Claims, 11 Drawing Sheets

Related U.S. Application Data

(60) Provisional application No. 62/197,188, filed on Jul. 27, 2015.

(52) U.S. Cl.
CPC ............... *A61F 2002/4622* (2013.01); *A61F 2002/4641* (2013.01)

(56) References Cited

U.S. PATENT DOCUMENTS

| | | | |
|---|---|---|---|
| 5,514,136 A * | 5/1996 | Richelsoph | A61F 2/4607 606/99 |
| 5,735,857 A * | 4/1998 | Lane | A61B 17/8872 606/207 |
| 6,322,564 B1 | 11/2001 | Surma | |
| 7,097,647 B2 | 8/2006 | Segler | |
| 7,608,112 B1 | 10/2009 | Kuczynski et al. | |
| 7,651,501 B2 | 1/2010 | Penenberg et al. | |
| 2004/0087944 A1 * | 5/2004 | Hazebrouck | A61F 2/4637 606/53 |
| 2004/0106927 A1 * | 6/2004 | Ruffner | A61B 17/025 606/90 |
| 2005/0222609 A1 | 10/2005 | Fankhauser et al. | |
| 2007/0005145 A1 | 1/2007 | Banks et al. | |
| 2007/0078464 A1 | 4/2007 | Jones et al. | |
| 2007/0100347 A1 * | 5/2007 | Stad | A61F 2/4611 606/90 |
| 2011/0218637 A1 | 9/2011 | Termanini | |
| 2014/0142583 A1 | 5/2014 | Fortin et al. | |

OTHER PUBLICATIONS

Written Opinion of the International Searching Authority for corresponding application PCT/US2016/042424 dated Oct. 4, 2016.

* cited by examiner

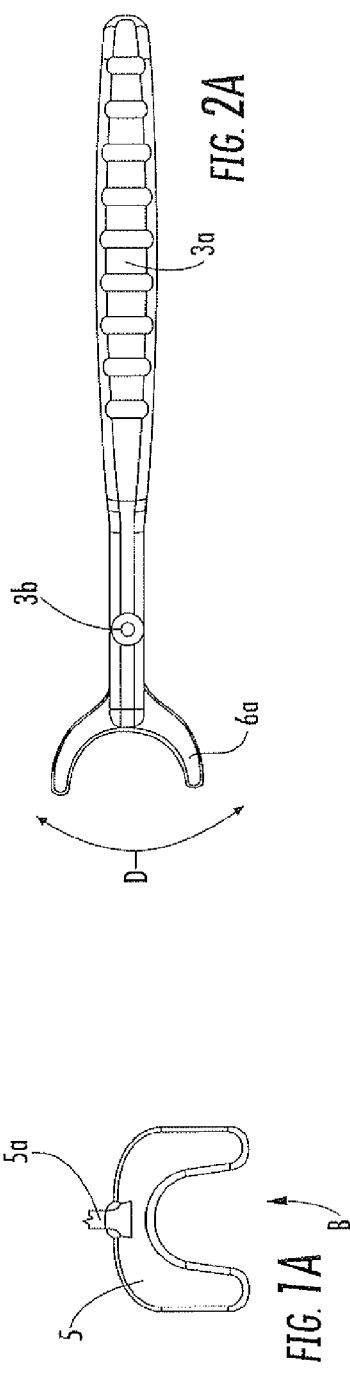
FIG. 1A
FIG. 1B
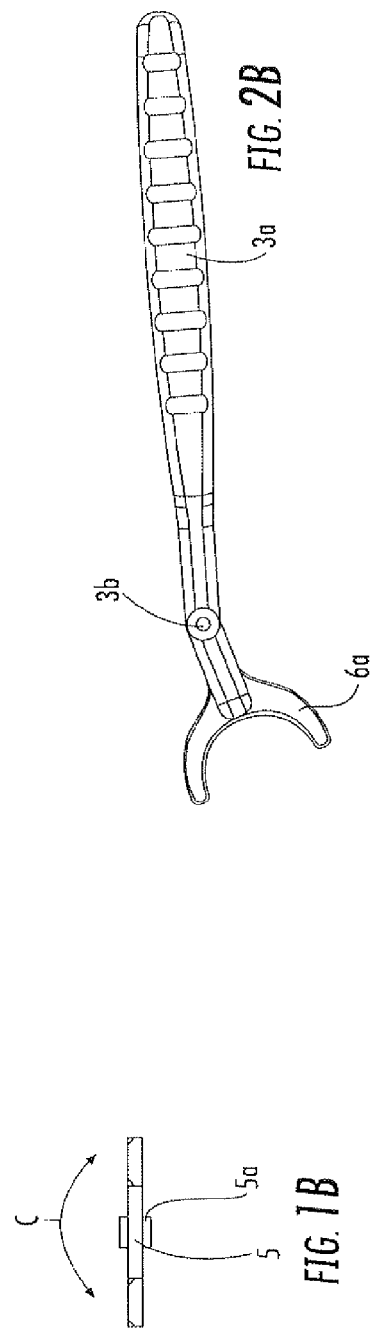
FIG. 2A
FIG. 2B

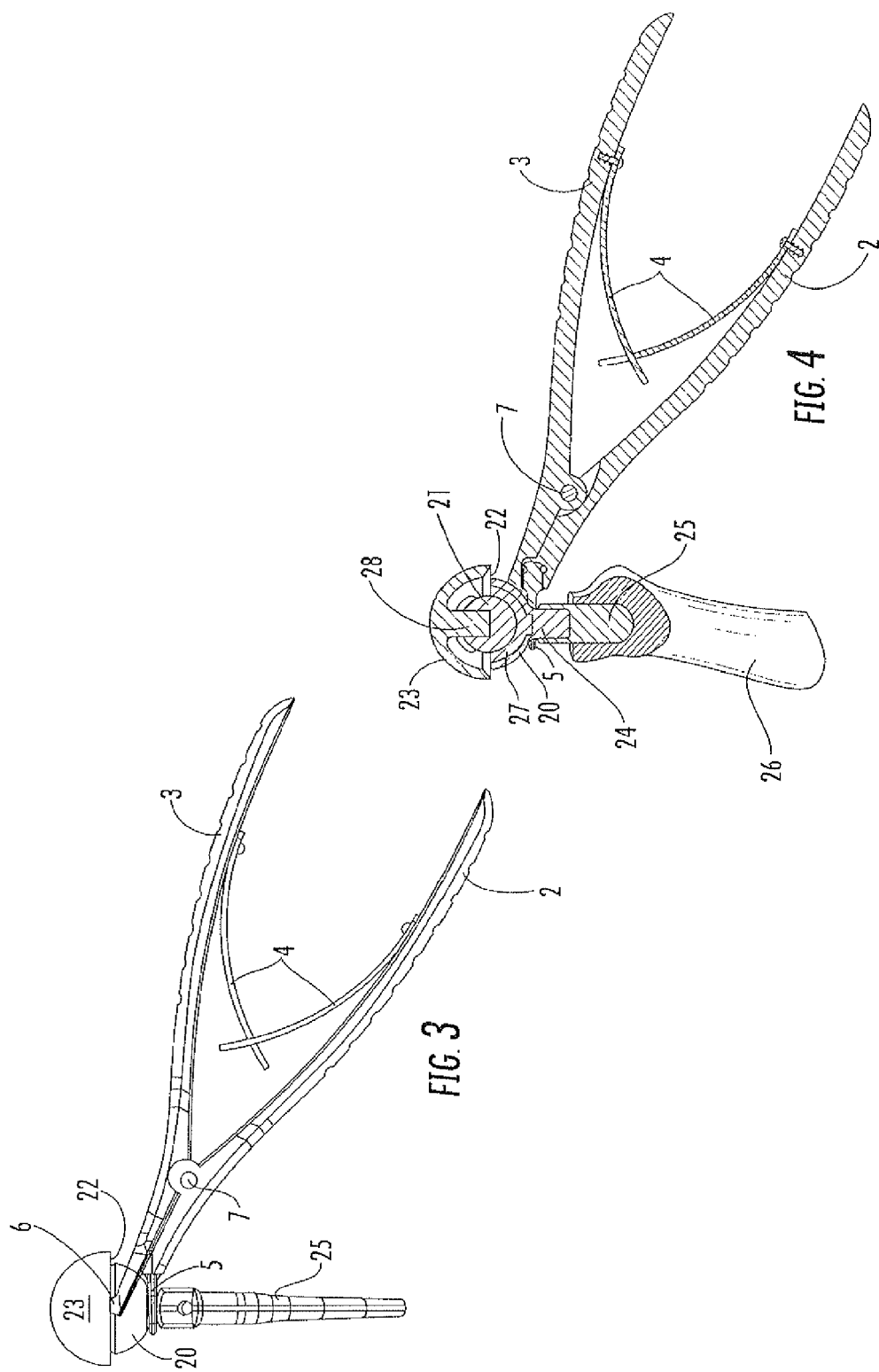

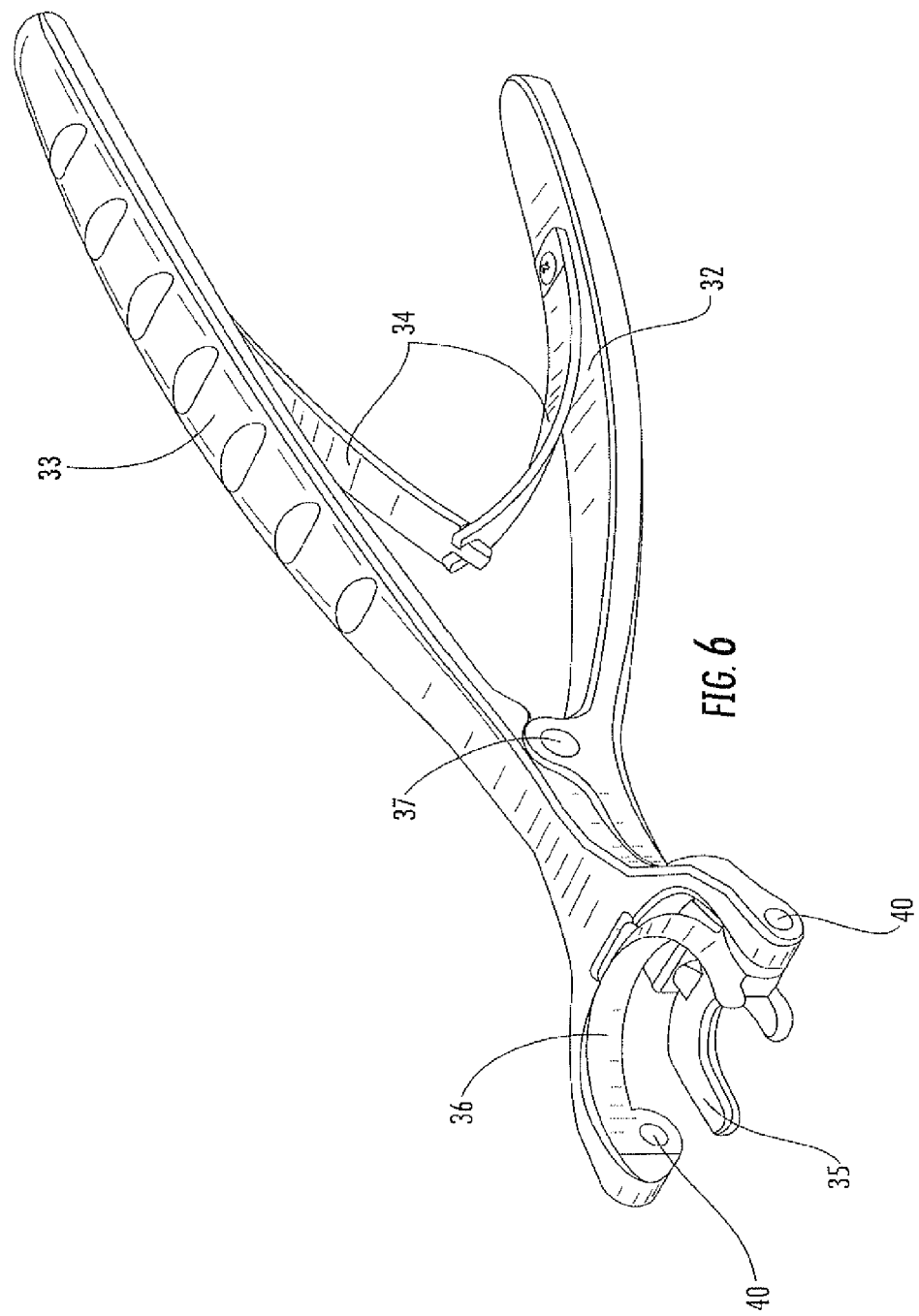

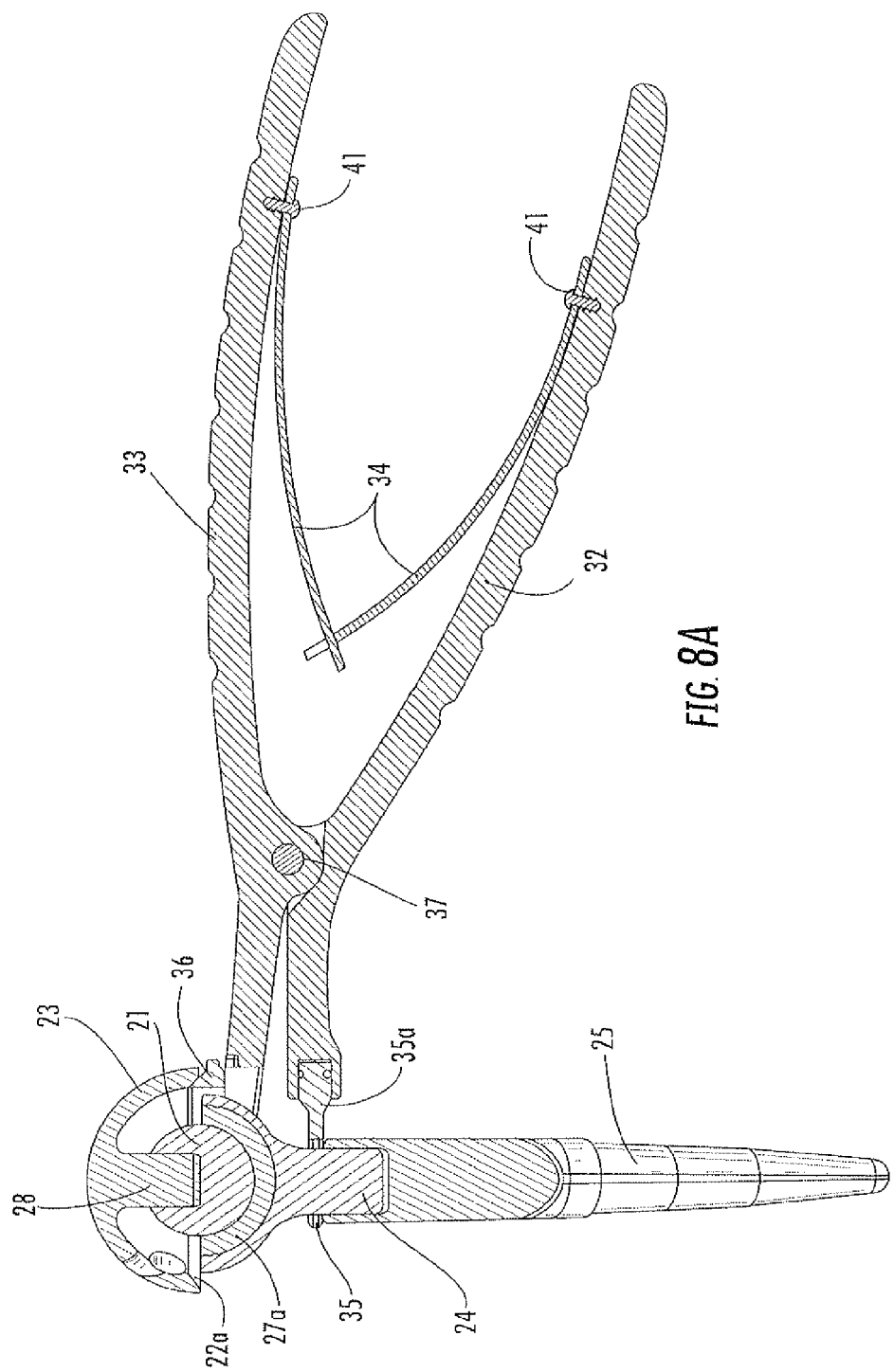

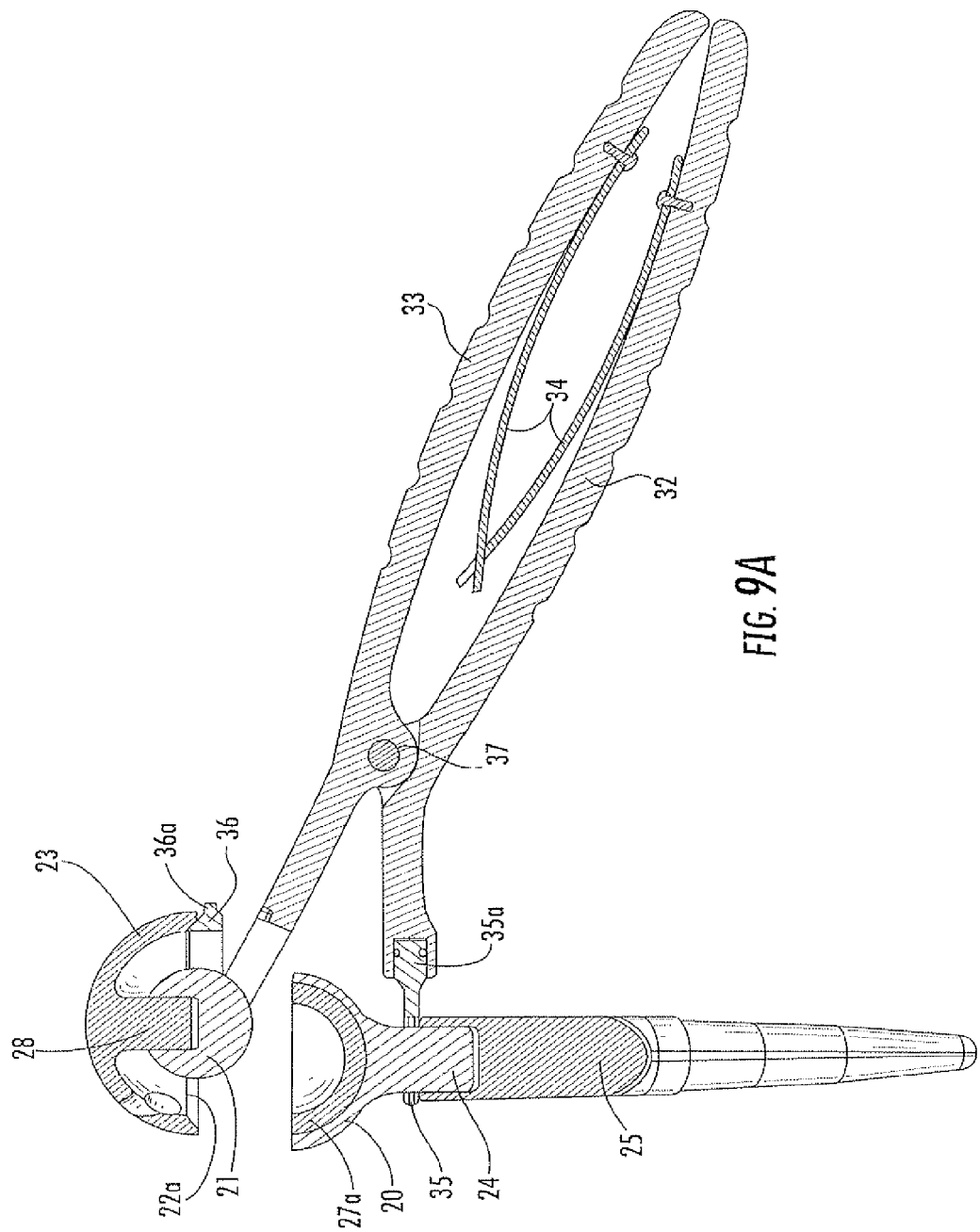

TOOL AND METHOD FOR SEPARATING A FEMORAL CUP FROM AN ACETABULAR BALL IN AN IMPLANTED HIP PROSTHESIS

This is a Divisional patent application based on U.S. Ser. No. 15/742,192 filed 5 Jan. 2018, which in turn is an application filed under 35 USC 371 based on PCT/US2016/042424 filed 15 Jul. 2016, which in turn claims priority to U.S. Ser. No. 62/197,188 filed 27 Jul. 2015. The present application claims the full priority benefit of these prior applications and herein incorporates by reference the full disclosures of these prior applications as if set forth herein.

BACKGROUND OF THE INVENTION

Field of the Invention

The present invention relates to surgical instruments used in connection with a hip prosthesis. More specifically, the invention has to do with surgical tools which are used to separate a femoral cup from an acetabular ball in an implanted hip replacement prosthesis.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, a femoral cup articulates on an acetabular ball when the prosthesis is implanted in a patient. The acetabular ball is affixed by means of a Morse taper to a stem which is affixed to and extends from the bottom of the concave surface of an acetabular cup. The surgical tools of the invention enable a surgeon to separate the femoral cup from the acetabular ball without pulling on the acetabular cup or the femoral implant and without disrupting any bone ingrowth. The surgical tool of the invention may be included as a component of a kit containing other surgical instruments and/or implant elements.

BRIEF DESCRIPTION OF THE DRAWINGS

FIG. 1A is a top elevation view of the femoral engagement component 5 of the first embodiment.

FIG. 1B is an end elevation view of FIG. 1A.

FIG. 2A is a bottom elevation view of an alternate embodiment of the second handle 3 of the first embodiment.

FIG. 2B is the same view as FIG. 2A following movement of the acetabular engagement component 6a.

FIG. 3 is a side elevation view of the tool of FIG. 2 positioned on a prosthesis just prior to separation of the femoral cup from the acetabular ball.

FIG. 4 is a section view of FIG. 3 with a partial section of a femur as an added element.

FIG. 6 is a perspective view of the second embodiment wherein the handles have not been squeezed toward one another.

FIG. 8A is a section view of FIG. 8.

FIG. 9A is a section view of FIG. 9.

DESCRIPTION OF THE PREFERRED EMBODIMENTS

Figure 1:
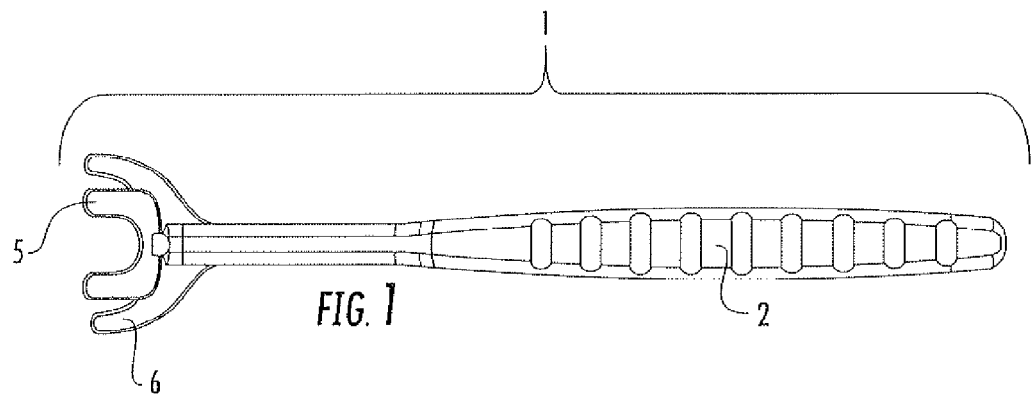
FIG. 1 is a top elevation view of a first embodiment of a surgical tool of the invention.
Figure 2:
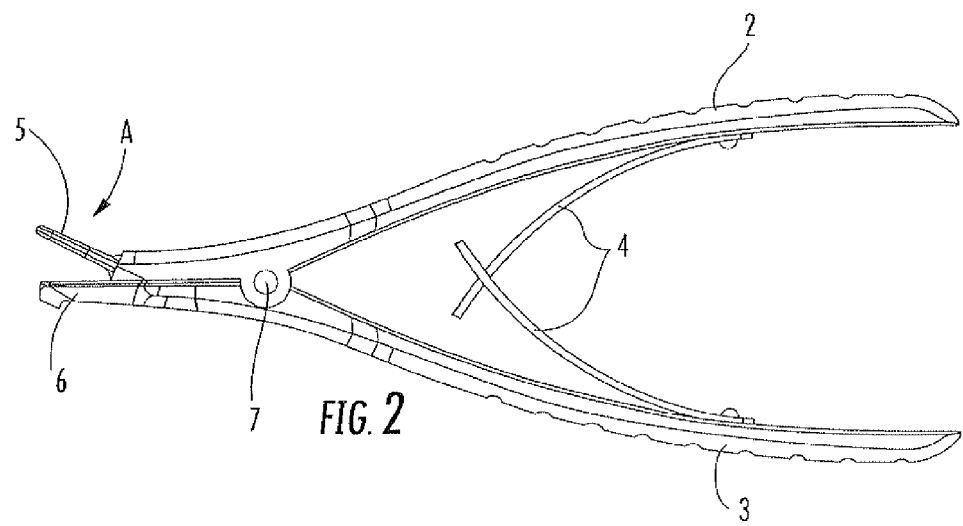
FIG. 2 is a side elevation view of the first embodiment of the surgical tool of the invention.

Referring to the first embodiment, the surgical tool 1 of the invention, also referred to herein as a surgical instrument, is illustrated in a top elevation view in FIG. 1 and a side elevation view in FIG. 2. The tool has a first handle 2 and a second handle 3. Springs 4 tend to bias the handles apart from one another as illustrated in FIG. 2. The distal end of the first handle 2 has a femoral engagement component 5 attached thereto and the distal end of the second handle 3 has an acetabular engagement component 6 attached thereto. Fulcrum pin 7 hinges the first handle 2 to the second handle 3 so that when the handles are squeezed toward one another the femoral engagement component 5 and the acetabular engagement component 6 are moved away from one another. The pin 7 thus provides a fulcrum between the first and second handles.

The femoral engagement component 5 illustrated in FIG. 1A is viewed from the direction of arrow A in FIG. 2. Femoral engagement component 5 may be rotatably connected to first handle 2 by means of axis pin 5a. Axis pin 5a allows a femoral engagement component 5 to rotate axially about the central axis of the first handle 2. In FIG. 1B, an end view of femoral engagement component 5 is illustrated as taken from the direction of arrow B in FIG. 1A. Arrow C in FIG. 1B illustrates the directions in which femoral engagement component 5 can be rotated.

FIGS. 2A and 2B illustrate a bottom elevation view of an alternate embodiment of the second handle which is designated as 3a. A hinge 3b is provided on handle 3a to allow lateral pivoting of a portion of the handle located between pin 7 (see FIG. 2) and acetabular engagement component 6a. Hinge 3b allows lateral movement in the directions of arrow D of FIG. 2A. FIG. 2B provides an example of a hinged handle 3a having an acetabular engagement component 6a at the distal end thereof.

In FIGS. 3 and 4 the surgical tool 1 is positioned on a prosthesis just prior to separation of the femoral cup 20 from the acetabular ball 21. The acetabular engagement component 6 is engaged with the circumferential edge 22 of acetabular cup 23 and the femoral engagement component 5 is engaged with the neck 24 of femoral cup 20, or the outer hemispherical surface of femoral cup 20, or both the neck 24 and the outer hemispherical surface of femoral cup 20. And the femoral engagement component 5 may also engage the top (i.e., the proximal end) of femoral implant 25 which is implanted in femur 26, shown in partial section. A liner 27 is illustrated in femoral cup 20. The acetabular ball 21 is affixed to stem 28 of the acetabular cup.

When handles 2 and 3 or 2 and 3a are squeezed toward one another, the femoral cup is separated from the acetabular ball.

The second embodiment of the surgical tool of the invention is very similar to the first embodiment except for the acetabular engagement element. This embodiment is illustrated in FIGS. 5-9A and it is designated as tool 31. A pivotable partial ring, referred to herein as acetabular engagement ring 36, is employed to engage the acetabular cup in the second embodiment as distinguished from acetabular engagement component 6 in the first embodiment. The term "acetabular engagement element" may be used herein to refer to both the acetabular engagement component 6 and the acetabular engagement ring 36.

Figure 5:
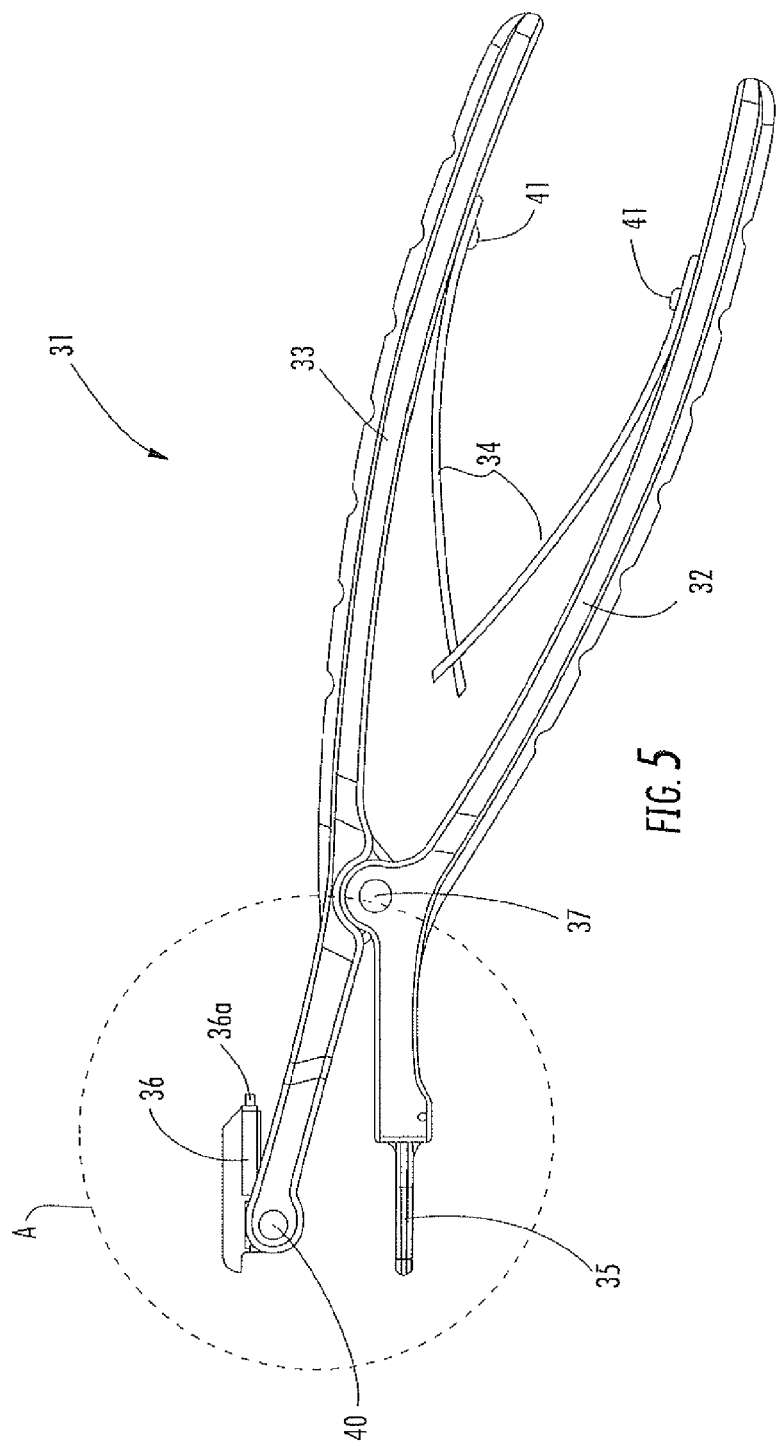
FIG. 5 is a side elevation view of a second embodiment of the tool of the invention wherein the handles have been squeezed toward one another.
Figure 5A:
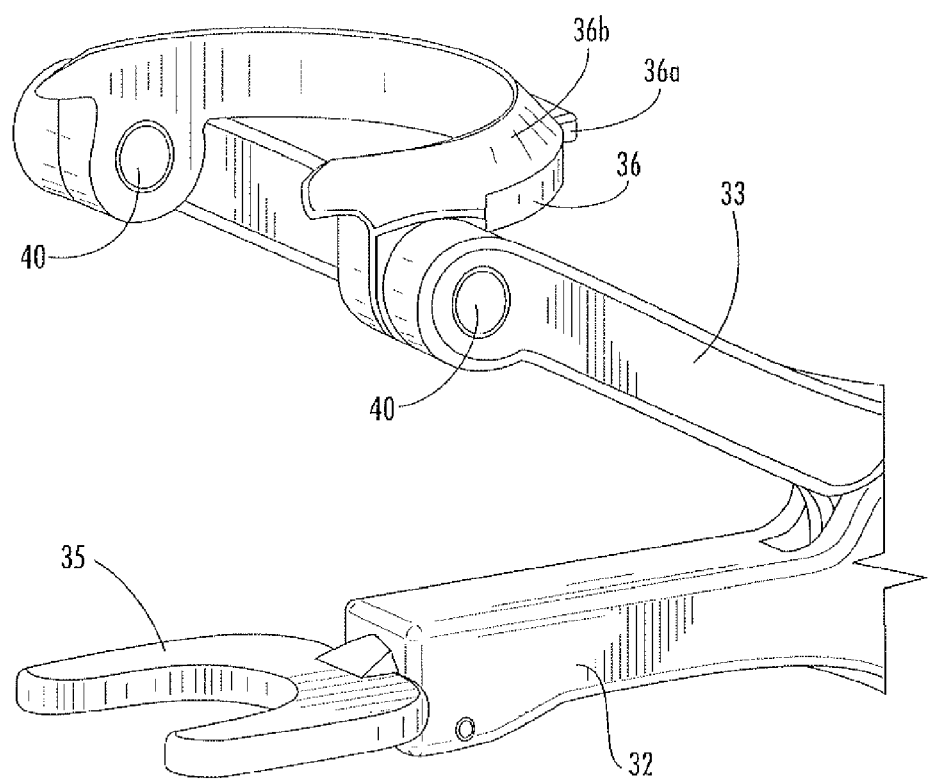
FIG. 5A is a perspective view of portion A of FIG. 5.
Figure 9:
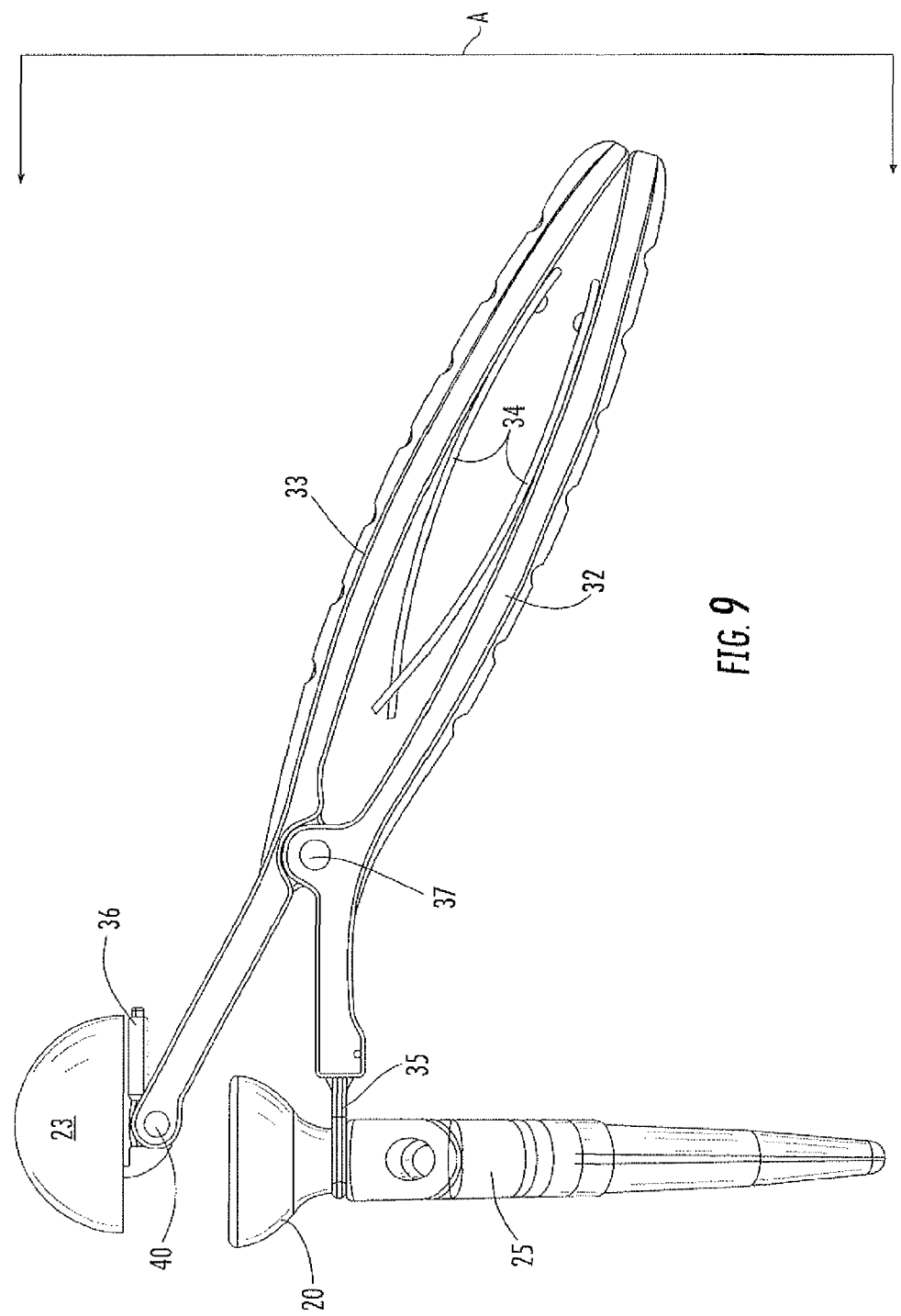
FIG. 9 is a side elevation view of the second embodiment engaged with a femoral implant/cup and an acetabular cup after the femoral cup and acetabular cup have been separated from one another.

FIG. 5 is a side elevation view of tool 31. The tool has a first handle 32 and a second handle 33. Springs 34, affixed to the handles with screws 41, tend to bias the handles apart from one another. And in FIG. 5, the handles have been squeezed toward one another to an intermediate position between fully open as shown in FIG. 6 and fully closed as shown in FIG. 9. The distal end of first handle 32 has a femoral engagement component 35 attached thereto. The distal end of second handle 33 has an acetabular engagement ring 36 pivotably attached thereto by means of ring pins 40. (See also FIG. 5A.) As can be seen from the drawings, ring 36 is pivotable about an axis which is perpendicular to the central axis of the distal portion of handle 33. Fulcrum pin 37 hinges the first handle 32 to the second handle 33 so that when the handles are squeezed toward one another the femoral engagement component 35 and the acetabular engagement ring 36 are moved away from one another. The pin 37 thus provides a fulcrum between the first and second handles.

As in the first embodiment, the femoral engagement component 35 of the second embodiment may be rotatably connected to first handle 32 by means of axis pin 35a. Axis pin 35a allows the femoral engagement component 35 to rotate axially about the central axis of the first handle 32 in the same manner as femoral engagement component 5 is allowed to rotate axially about the central axis of first handle 2 in the first embodiment. The alternate embodiment of second handle 3a which has a hinge 3b as described above (See FIG. 2B) can also be used with the second embodiment of the tool of the invention.

Figure 7:
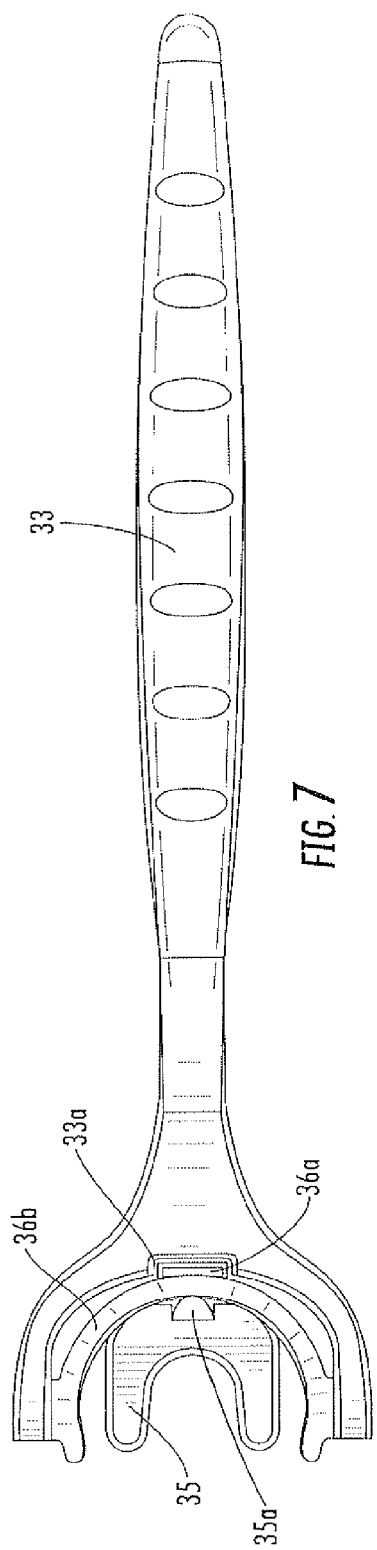
FIG. 7 is a top elevation view of FIG. 6.

Referring to FIGS. 5A, 7, 8A and 9A, acetabular engagement ring 36 has a beveled edge 36b which engages beveled edge 22a of acetabular cup 23. Ring 36 also has a tab 36a which is seated in indent 33a to prevent downward rotation of ring 36 below the horizontal central plane of the distal end of handle 33. Thus, as can be seen in FIGS. 6 and 7 wherein the handles are in the fully open position, tab 36a is seated in indent 33a and ring 36 is prevented from downward rotation in that position.

Figure 8:
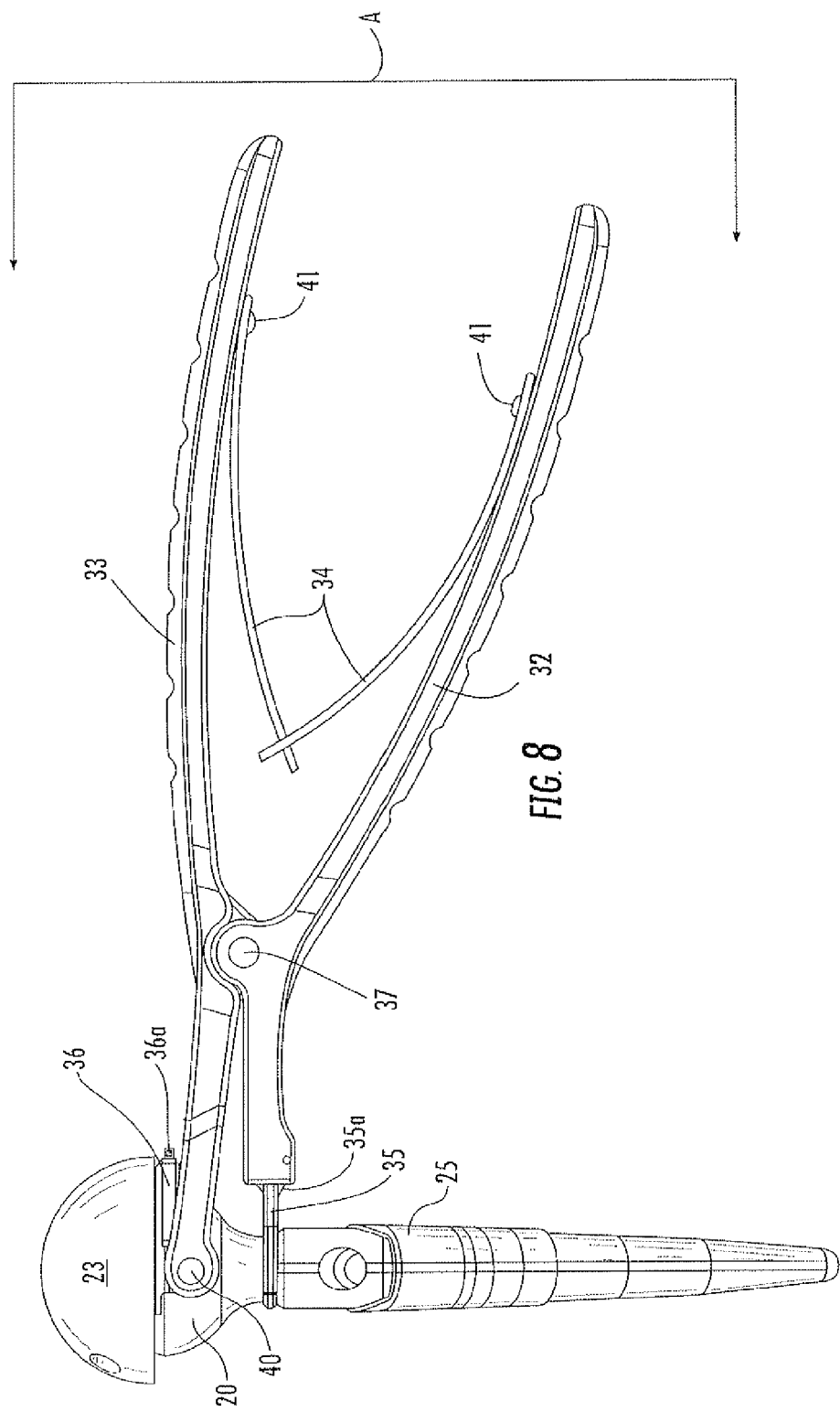
FIG. 8 is a side elevation view of the second embodiment engaged with a femoral implant/cup and an acetabular cup before the femoral cup and acetabular cup are separated from one another.

In FIGS. 8 and 8A the surgical tool 31 is positioned on a prosthesis just prior to separation of the femoral cup 20 from the acetabular ball 21. The beveled edge 36b of acetabular engagement ring 36 is engaged with the circumferential beveled edge 22a of acetabular cup 23 and the femoral engagement component 35 is engaged with the neck 24 of femoral cup 20 or the outer hemispherical surface of femoral cup 20, or both the neck 24 and the outer hemispherical surface of femoral cup 20. A femoral implant 25 is also illustrated and the femoral engagement component 35 may also engage the top (i.e., the proximal end) of implant 25. A liner 27 is illustrated in femoral cup 20. The acetabular ball 21 is affixed to stem 28 of the acetabular cup.

When handles 32 and 33 are squeezed toward one another the femoral cup is separated from the acetabular ball as shown in FIGS. 9 and 9a.

In the surgical method of the invention, femoral engagement component 5 or 35 is engaged with the neck of the femoral cup, or an outer hemispherical surface of the femoral cup or both the neck and the outer hemispherical surface of the femoral cup and/or the upper surface (i.e. the proximal end) of a femoral implant. Simultaneously, the acetabular engagement component 6 is engaged with the circumferential edge 22 of the acetabular cup 23, or the circumferential beveled edge 36b of femoral engagement ring 36 is engaged with the circumferential beveled edge 22a of acetabular cup 23, and then the first and second handles are squeezed toward one another thereby causing the femoral cup and the acetabular ball to be separated from one another.

The invention claimed is:

1. A surgical tool configured to separate a femoral cup upon a femoral stem from an acetabular ball engaging the femoral cup, the acetabular ball mounted upon a stem affixed to a concave surface of an acetabular cup having a circumferential edge, the stem extending outwardly from an interior of said acetabular cup of a hip prosthesis, the surgical tool comprising:

a first handle and a second handle connected by a single fulcrum pin in a hinged rotational relationship about the single fulcrum pin in a rotational plane perpendicular to an axis of the single fulcrum pin, the first and second handles being urged apart by a spring, each handle having a proximal end and a distal end;

the first handle having a femoral engagement component at its distal end thereof, the femoral engagement component having a generally flat, U-shaped plate configuration having a pair of side legs joined at a base connecting the femoral engagement component to the distal end of the first handle, and wherein the U-shaped plate is within a first plane; and the second handle having an acetabular engagement element at its distal end thereof, the acetabular engagement element is an acetabular engagement component having a generally flat, U-shaped plate configuration having a pair of side legs joined at a base connecting the acetabular engagement component to the distal end of the second handle, and wherein the U-shaped plate of the acetabular engagement component is within a second plane, the femoral engagement component being sized to engage a neck of a femoral cup, engage an outer hemispherical surface of the femoral cup, engage both the neck and the outer hemispherical surface of the femoral cup, or engage a proximal end of a femoral stem, and the acetabular engagement element being sized to engage at least a part of the circumferential edge of the acetabular cup, wherein the second plane of the acetabular engagement element forms a first angle with the first plane of the femoral engagement component when the surgical tool is in a first configuration when the proximal ends of the first and second handles are spaced apart at a maximum distance, and when the surgical tool is in a second configuration and the proximal ends of the first and second handles are at a lesser spaced apart distance than in the first configuration, the second plane of the acetabular engagement element forms a second angle with the first plane of the femoral engagement component, wherein the second angle is greater than the first angle.

2. The surgical tool of claim 1 further comprising a hinge disposed between the fulcrum pin and the acetabular engagement element, the hinge being arranged to allow lateral pivoting of the acetabular engagement element.

3. The surgical tool of claim 1 wherein the acetabular engagement element is an acetabular engagement ring which is pivotally attached between two parts at the distal end of the second handle which two parts are within the second plane.

4. A method of using the surgical tool of claim 3 in separating a femoral cup upon a femoral stem from an acetabular ball engaging the femoral cup, the acetabular ball mounted upon a stem affixed to a concave surface of an acetabular cup having a circumferential edge, the stem extending outwardly from an interior of the acetabular cup of a hip prosthesis comprising the steps of: engaging the femoral engagement component with a femoral implant component while simultaneously engaging the acetabular engagement ring with an acetabular implant component and then squeezing the first and second handles towards one another thereby causing the femoral implant component and the acetabular implant component to be separated from one another, wherein the femoral implant component comprises a neck of a femoral cup, an outer hemispherical surface of the femoral cup, both the neck and the outer hemispherical surface of the femoral cup or a proximal end of a femoral implant.

5. A kit containing the surgical tool of claim 1 and at least one further surgical instrument or at least one further implant element.

6. A method of using the surgical tool of claim 1 in separating a femoral cup upon a femoral stem from an acetabular ball engaging the femoral cup, the acetabular ball mounted upon a stem affixed to a concave surface of an acetabular cup having a circumferential edge, the stem extending outwardly from an interior of the acetabular cup of a hip prosthesis comprising the steps of:
engaging the femoral engagement component with a femoral implant component while simultaneously engaging the acetabular engagement element with an acetabular implant component, and squeezing the first and second handles towards one another and thereby causing the femoral implant component and the acetabular implant component to be separated from one another, wherein the femoral implant component comprises a neck of a femoral cup, an outer hemispherical surface of the femoral cup, both the neck and the outer hemispherical surface of the femoral cup or a proximal end of a femoral implant.

7. The surgical tool of claim 1, wherein the femoral engagement component is rotatably connected to the distal end of the first handle, the femoral engagement component having an axis of rotation substantially perpendicular to the axis of the single fulcrum pin.

8. The surgical tool of claim 1, wherein the disposition of the fulcrum pin between the distal and proximal ends of each handle provides only for rotational movement of the distal ends when the proximal ends of each of the handles are moved towards one another.

\* \* \* \* \*